US007776321B2

(12) United States Patent
Cascalho et al.

(10) Patent No.: US 7,776,321 B2
(45) Date of Patent: Aug. 17, 2010

(54) MUTABLE VACCINES

(75) Inventors: Marilia I. Cascalho, Rochester, MN (US); Jeffrey L. Platt, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 399 days.

(21) Appl. No.: 10/491,026

(22) PCT Filed: Sep. 24, 2002

(86) PCT No.: PCT/US02/30146

§ 371 (c)(1),
(2), (4) Date: Mar. 25, 2004

(87) PCT Pub. No.: WO03/045304

PCT Pub. Date: Jun. 5, 2003

(65) Prior Publication Data

US 2004/0242517 A1    Dec. 2, 2004

Related U.S. Application Data

(60) Provisional application No. 60/325,041, filed on Sep. 26, 2001, provisional application No. 60/336,863, filed on Nov. 2, 2001.

(51) Int. Cl.
 *A61K 48/00* (2006.01)
(52) U.S. Cl. .................................. 424/93.2; 424/93.21
(58) Field of Classification Search ........................ None
See application file for complete search history.

(56) References Cited

U.S. PATENT DOCUMENTS

| 4,873,316 | A |   | 10/1989 | Meade et al. |        |
|-----------|---|---|---------|--------------|--------|
| 5,238,820 | A | * | 8/1993  | Kaufman ...... | 435/69.1 |
| 5,885,827 | A |   | 3/1999  | Wabl et al.  |        |
| 5,928,913 | A |   | 7/1999  | Efstathiou et al. |   |
| 6,013,473 | A |   | 1/2000  | Wei          |        |
| 6,270,795 | B1 |  | 8/2001  | Jones et al. |        |
| 6,713,279 | B1 | * | 3/2004 | Short ......... | 435/69.1 |

FOREIGN PATENT DOCUMENTS

| EP | 0 161 640 | 11/1985 |
| EP | 0 248 531 | 12/1987 |
| EP | 0 475 178 | 3/1992 |
| EP | 0 264 166 | 8/1996 |
| WO | WO 94/23738 | 10/1994 |
| WO | WO 95/05853 | 3/1995 |

OTHER PUBLICATIONS

Korber et al, Brit Med Bull 2001;58:19-42.*
Yang et al, Genetics, 2000;155;431-449.*
Jacobs et al, Curr Opin Immunol 2001;13:208-18.*
Hilleman, Vaccine 2002;20:3068-87.*
Ross, Nat Immunol 2000;127;1:127-31.*
Bachl and Wabl, "An immunoglobulin mutator that targets G•C base pairs," *Proc. Natl. Acad. Sci. USA*, 1996, 93:851-855.
Bachl et al., "The Ig mutator is dependent on the presence, position, and orientation of the large intron enhancer," *Proc. Natl. Acad. Sci. USA*, 1998, 95:2396-2399.
Bachl et al., "An experimental solution for the Luria-Delbrück fluctuation problem in measuring hypermutation rates," *Proc. Natl. Acad. Sci. USA*, 1999, 96:6847-6849.
Bachl et al., "Increased Transcription Levels Induce Higher Mutation Rates in a Hypermutating Cell Line," *J. Immunol.*, 2001, 166:5051-5057.
Camper and Tilghman, "Postnatal repression of the alpha-fetoprotein gene is enhancer independent," *Genes. Dev.*, 1989, 3:537-546.
Baldari et al., "A novel leader peptide which allows efficient secretion of a fragment of human interleukin 1β in *Saccharomyces cerevisiae*," *EMBO J.*, 1987, 6(1):229-234.
Banerji et al., "A Lymphocyte-Specific Cellular Enhancer Is Located Downstream of the Joining Region in Immunoglobulin Heavy Chain Genes," *Cell*, 1983, 33:729-740.
Barbour and Restrepo, "Antigenic Variation in Vector-Borne Pathogens," *Emerg. Infect. Dis.*, 2000, 6(5):449-457.
Brunelli and Pall, "A Series of Yeast/*Escherichia coli* λ Expression Vectors Designed for Directional Cloning of cDNAs and *cre / lox*-Mediated Plasmid Excision," *Yeast*, 1993, 9:1309-1318.
Brunelli and Pall, "A Series of Yeast Shuttle Vectors for Expression of cDNAs and Other DNA Sequences," *Yeast*, 1993, 9:1299-1308.
Burrows et al., "Expression of μ and γ immunoglobulin heavy chains in different cells of a cloned mouse lymphoid line," *Proc. Natl. Acad. Sci. USA*, 1981, 78(1):564-568.
Byrne and Ruddle, "Multiplex gene regulation: A two-tiered approach to transgene regulation in transgenic mice," *Proc. Natl. Acad. Sci. USA*, 1989, 86:5473-5477.
Calame and Eaton, "Transcriptional Controlling Elements in the Immunoglobulin and T Cell Receptor Loci," *Adv. Immunol.*, 1988, 43:235-275.

(Continued)

*Primary Examiner*—Q. Janice Li
(74) *Attorney, Agent, or Firm*—Casimir Jones, S.C.

(57) ABSTRACT

The invention relates to methods and materials useful for targeting antigenic determinants of mutable pathogens for somatic hypermutation. These methods and materials can be used to induce an immune response against antigenic variants of mutable pathogens.

3 Claims, 2 Drawing Sheets

OTHER PUBLICATIONS

Deitsch et al., "Shared Themes of Antigenic Variation and Virulence in Bacterial, Protozoal, and Fungal Infections," *Microbiol. Mol. Biol. Rev.*, 1997, 61(3):281-293.

Dempsey et al., "C3d of Complement as a Molecular Adjuvant: Bridging Innate and Acquired Immunity," *Science*, 1996, 271:348-350.

Edlund et al., "Cell-Specific Expression of the Rat Insulin Gene: Evidence for Role of Two Distinct 5' Flanking Elements," *Science*, 1985, 230:912-916.

Gottesman, "Minimizing Proteolysis in *Escherichia coli*: Genetic Solutions," *Meth. Enzymol.*, 1990, 185:119-129.

Grosschedl et al., "Introduction of a µ Immunoglobulin Gene into the Mouse Germ Line: Specific Expression in Lymphoid Cells and Synthesis of Functional Antibody," *Cell*, 1984, 38:647-658.

Grosschedl and Baltimore, "Cell-Type Specificity of Immunoglobulin Gene Expression is Regulated by at Least Three DNA Sequence Elements," *Cell*, 1985, 41:885-897.

Kaufman et al., "Translational efficiency of polycistronic mRNAs and their utilization to express heterologous genes in mammalian cells," *EMBO J.*, 1987, 6:187-195.

Kessel and Gruss, "Murine Developmental Control Genes," *Science*, 1990, 249:374-379.

Kurjan and Herskowitz, "Structure of a Yeast Pheromone Gene (*MFα*): A Putative α-Factor Precursor Contains Four Tandem Copies of Mature α-Factor," *Cell*, 1982, 30:933-943.

Luckow and Summers, "High Level Expression of Nonfused Foreign Genes with *Autographa californica* Nuclear Polyhedrosis Virus Expression Vectors," *Virology*, 1989, 170:31-39.

Paige et al., "Independent control of immunoglobulin heavy and light chain expression in a murine pre-B-cell line," *Nature*, 1981, 292:631-633.

Meyer and Neuberger, "The immunoglobulin κ locus contains a second, stronger B-cell-specific enhancer which is located downstream of the constant region," *EMBO J.*, 1989, 8(7):1959-1964.

Pinkert et al., "An albumin enhancer located 10kb upstream functions along with its promoter to direct efficient, liver-specific expression in transgenic mice," *Genes Dev.*, 1987, 1:268-276.

Queen and Baltimore, "Immunoglobulin Gene Transcription Is Activated by Downstream Sequence Elements," *Cell*, 1983, 33:741-748.

Ross et al., "C3d enhancement of antibodies to hemagglutinin accelerates protection against influenza virus challenge," *Nat. Immunol.*, 2000, 1(2):127-131.

Schultz et al., "Expression and secretion in yeast of a 400-kDa envelope glycoprotein derived from Epstein-Barr virus," *Gene*, 1987, 54:113-123.

Seed, "An LFA-3 cDNA encodes a phospholipid-linked membrane protein homologous to its receptor CD2," *Nature*, 1987, 329:840-842.

Siden and Baltimore, "Immunoglobulin Synthesis by Lymphoid Cells Transformed in Vitro by Abelson Murine Leukemia Virus," *Cell*, 1979, 16:389-396.

Smith et al., "Production of Human Beta Interferon in Insect Cells Infected with a Baculovirus Expression Vector," *Mol. Cell. Biol.*, 1983, 3(12):2156-2165.

Wada et al., "Codon usage tabulated from the GenBank genetic sequence data," *Nucl. Acids Res.*, 1992, 20:2111-2118.

Winoto and Baltimore, "A novel, inducible and T cell-specific enhancer located at the 3' end of the T cell receptor α locus," *EMBO J.*, 1989, 8(3):729-733.

* cited by examiner

MUTABLE VACCINES

This application is a National Stage Application under 35 U.S.C. §371 that claims the benefit of Application Ser. No. PCT/US02/30146, filed Sep. 24, 2002, which claims the benefit of U.S. Provisional Application Ser. No. 60/336,863, filed Nov. 2, 2001, now expired, and the benefit of U.S. Provisional Application Ser. No. 60/325,041, filed Sep. 26, 2001, now expired.

TECHNICAL FIELD

This invention relates to methods and materials that can be used to induce an immune response against antigenic variants of mutable pathogens. In particular, the invention pertains to nucleic acid constructs that can target antigenic determinants of mutable pathogens for somatic hypermutation.

BACKGROUND

Vaccination plays an important role in preventing infectious diseases. For example, vaccination strategies have proven successful in eradicating smallpox and in diminishing the incidence of many other infectious diseases worldwide. Traditional vaccination methods employ pathogens' antigens as immunogens. In one traditional approach, antigens of infectious organisms are introduced into a host. In a variation of this approach, DNA encoding an antigen of an infectious organism is introduced into a host, and the host makes antigens to which the immune system responds.

The fixed nature of a traditional vaccine can be a major limitation to its success in preventing diseases caused by mutable pathogens (e.g., influenza, HIV, hepatitis C). When pathogens mutate to form antigenic variants, an immune response directed to non-mutated organisms can be obsolete and ineffective. Because immune responses typically develop much more slowly than new variants proliferate, mutable pathogens can rapidly spread through populations.

The current strategy used to prevent infectious diseases caused by mutable pathogens is to vaccinate repeatedly, each time a new strain is identified. The current approach has several drawbacks. First, since the nature of spontaneous variants cannot be predicted, repeated vaccination cannot proactively protect against these variants. Second, repeated vaccination requires frequent administration and raises concerns about compliance. Third, extensive vaccination of the population for new pathogen variants increases the selection pressure for more virulent mutants and could lead to pandemics.

SUMMARY

The invention features methods and materials for targeting the genes of antigenic determinants of mutable pathogens for somatic hypermutation. The methods and materials of the invention facilitate the production of variant antigenic determinants and corresponding antibodies in a host, and thereby promote an immune response against antigenic variants of mutable pathogens.

The invention provides nucleic acid constructs having a nucleic acid that encodes an antigenic determinant of a mutable pathogen operably linked to a promoter and to one or more hypermutability elements. In some embodiments, the nucleic acid encodes a hepatitis C, influenza, HIV, *Candida albicans*, *Borrelia* spp., *Anaplasma marginale*, *Neisseria meningitides*, *Neisseria gonorrhoeae*, *Escherichia coli.*, *Salmonella* spp., *Streptococcus pyogenes*, African trypanosome, *Plasmodium falciparum*, or *Babesia bovis* antigenic determinant. In some embodiments, the nucleic acid encodes an influenza hemagglutinin polypeptide, an HIV Env polypeptide, an HIV gp 120 polypeptide, a hepatitis C, E1 or E2 polypeptide, a Candida albicans PEP1 polypeptide, a *Neisseria meningitides* or *Neisseria gonorrhoeae* pilin protein, a *Streptococcus pyogenes* M protein, an African trypanosome VSG polypeptide, a *Borrelia* spp. VSM polypeptide, a *Plasmodium falciparum* PfEMP1 polypeptide, or an antigenic portion of any one of these proteins.

The invention also provides isolated cells containing a nucleic acid construct having a nucleic acid that encodes an antigenic determinant of a mutable pathogen operably linked to a promoter and to one or more hypermutability elements. In some embodiments, the cell is a hypermutable cell (e.g., a hypermutable B cell).

In another aspect, the invention provides methods for making variant antigenic polypeptides. The methods involve: a) introducing a nucleic acid construct having a nucleic acid that encodes an antigenic determinant of a mutable pathogen operably linked to a promoter and to one or more hypermutability elements into a hypermutable cell; and b) isolating a variant of the encoded antigenic determinant.

The invention further provides methods for making variant antigenic polypeptides in a mammal. The methods involve a) introducing a nucleic acid construct having a nucleic acid that encodes an antigenic determinant of a mutable pathogen operably linked to a promoter and to one or more hypermutability elements into a mammal; and b) isolating a variant of the encoded antigenic determinant.

In yet another aspect, the invention provides methods for inducing an immune response in a mammal. The methods involve: a) introducing a nucleic acid construct having a nucleic acid that encodes an antigenic determinant of a mutable pathogen operably linked to a promoter and to one or more hypermutability elements into a mammal; and b) determining that the mammal produces antibodies against a variant of the encoded antigenic determinant.

Unless otherwise defined, all technical and scientific terms used herein have the meaning generally understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, controls. In addition, the materials, methods, and examples are illustrative and are not intended to be limiting.

Other features and advantages of the invention will be apparent from the following detailed description, and from the claims.

DETAILED DESCRIPTION

Figure 1:
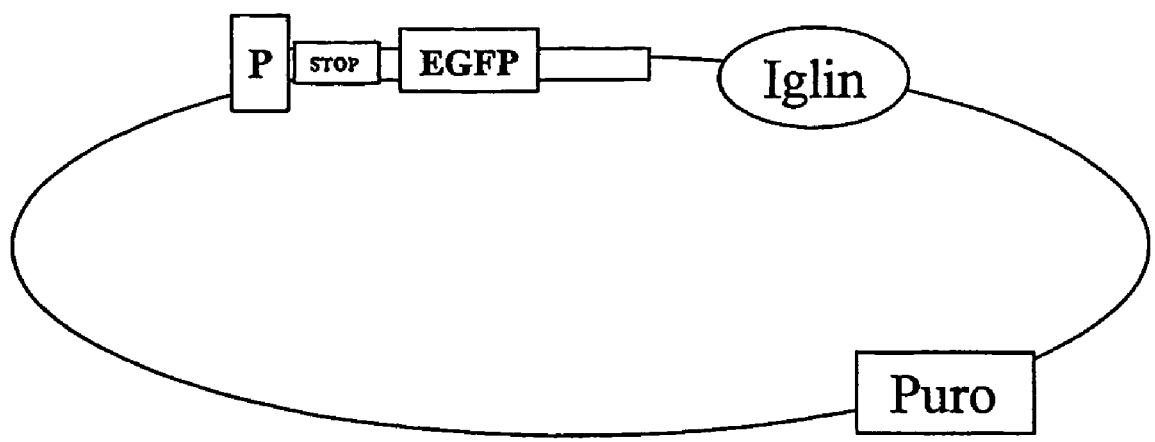
FIG. 1 is a schematic illustration of a DNA construct.

In general, the invention provides nucleic acid constructs that can target antigenic polypeptides of mutable pathogens for somatic hypermutation, a cellular process by which mutagenesis of a nucleic acid occurs at a rate approaching that naturally occurring in the immunoglobulin variable region, when introduced into a mammal. Mutable pathogens can evade the immune system of an infected mammal by mutating to form an antigenic variant (i.e., a variant having altered antigenic determinants). Such antigenic variation arises in individual clones or genomes in a host and can involve "the loss, gain, or change in a particular antigenic group, usually by loss, gain, or change in one of the polypeptide or polysaccharide antigens." See, Beale G. H (1961) *Ann Rev Microbiol* 15:263-296. The adaptive immune system of an infected vertebrate selects against the original infecting serotype, but that response is often ineffective against new variants—thus creating a selection pressure favorable to mutants.

Mutable pathogens can be bacterial, protozoal, fungal, or viral in nature. Bacterial, protozoal and fungal antigenic variation generally involves modification of transcript levels, gene conversion, DNA rearrangement, and/or multiple point mutations. See e.g., Barbour, A. G. and Restrepo, B. I (2000) *Emerg Infect Dis*. 6:449-57; Deitsch K. W. et al. (1997) *Microbiol Mol Biol Rev* 61:281-293. Antigenic variation in viruses typically involves the accumulation of point mutations in a single genotype (e.g., the antigenic drift of influenza A virus, and the generation of quasi-species of hepatitis C virus) or the recombination or reassortment between two different genotypes infecting the same host (e.g., antigenic shift of influenza A virus). Mutable bacterial pathogens include, for example, *Borrelia* spp., *Anaplasma marginale*, *Neisseria meningitides*, *Neisseria gonorrhoeae*, *Escherichia coli*, *Salmonella* spp, *Streptococcus pyogenes*. Mutable protozoal pathogens include, for example, African trypanosomes, *Plasinodium falciparum* and *Babesia bovis*. *Candida albicans* is an exemplary mutable flngal pathogen. Mutable viral pathogens include, for example, influenza, HIV, and hepatitis C.

As used herein, the term mutable pathogen also includes pathogens that have been genetically engineered such that one or more antigenic determinants are altered relative to that of naturally occurring serotypes (e.g., altered to avoid antibiotics effective against known serotypes). Non-limiting examples of bacterial and viral pathogens as well as other eukaryotic pathogens that may be genetically altered include Crimean-Congo hemorrhagic fever virus, Eastern equine encephalitis virus, Ebola virus, equine morbillivirus, Lassa fever virus, Marburg virus, Rift Valley fever virus, South American hemorrhagic fever (Junin, Machopa, Sabia, Flexal, Guanarito), tickborne encephalitis complex viruses, variola major virus (smallpox virus), Venezuelan equine encephalitis virus, viruses causing hantavirus pulmonary syndrome, yellow fever virus, Bacillus anthracis, *Brucella abortus*, *Brucella melitensis*, *Brucella suis*, *Burkholderia* (*Pseudomonas*) *mallei*, *Burkholderia* (*Pseudomonas*) *pseudomallei*, *Clostridium botulinuin*, *Francisella tularensis*, *Yersinia pestis*, *Rickettsiae*, *Coxiella burnetii*, *Rickettsia prowazekii*, *Rickettsia rickettsii*, and *Coccidioides iminitis*. Other pathogens, such as *Clostridiun perfringens*, *Salmonella typhimuriun*, *Ascaris lumbricocoides*, *Giardia lamblia*, *Shigella dysenteriae* and *Vibrio cholerae* also can be genetically engineered to have altered antigenic determinants.

Nucleic acid constructs of the invention can be used to induce an immune response against mutable pathogens as well as antigenic variants thereof. A mammal containing such nucleic acid constructs will develop an immunological record of the encoded antigen and variants thereof. Because immunological memory of antigenic variants precedes infection, the odds that a mutable pathogen will evade the mammal's immune response are diminished.

Nucleic Acid Constructs

As indicated above, nucleic acid constructs of the invention contain a nucleic acid encoding an antigenic determinant of a mutable pathogen. Nucleic acid constructs of the invention are not naturally present in living organisms.

An antigenic determinant is a polypeptide of a pathogen that can elicit an immune response, either alone or in association with an adjuvant, in a mammal. An antigenic determinant is at least 6 amino acids in length. Thus, antigenic determinants can be full-length polypeptides, as well as antigenic portions thereof. Exemplary antigenic determinants include hemaglutinin of influenza, Env of HIV, gp 120 of HIV, E1 and E2 of hepatitis C, PEP1 of *Candida albicans*, pilin proteins of *Neisseria meningitides* and *Neisseria gonorrhoeae*, M protein of *Streptococcus pyogenes*, variant-specific glycoproteins (VSG) of African trypanosomes, variant major protein (VSM) of *Borrelia* spp., PfEMP1 proteins of *Plasmodium falciparum* and antigenic portions thereof. Additional antigenic determinants include lethal factor, edema factor, and protective antigen of *B. anthracis*, and antigenic portions thereof. Nucleic acids encoding presently known antigenic determinants, as well as variants thereof, are suitable for constructs of the invention.

In some embodiments, the coding sequence for an antigenic determinant is contiguous with a nucleic acid sequence encoding one or more complement C3d polypeptides or portions thereof. Complement peptides such as C3d can increase the immunogenicity of associated antigens. See e.g., Dempsrey et al. (1996) *Nature* 271:348-350.

A nucleic acid encoding an antigenic determinant is operably linked to at least one hypermutability element. A hypermutability element is a nucleic acid that acts in cis to facilitate somatic hypermutation of another nucleic acid (i.e., a subject nucleic acid). With respect to a hypermutability element, "operably linked" refers to positioning of a hypermutability element in a nucleic acid construct relative to a promoter and a subject nucleic acid in such a way as to facilitate somatic hypermutation of the subject nucleic acid sequence. A nucleic acid construct that contains a hypermutability element operably linked to a subject nucleic acid (e.g., a nucleic acid encoding an antigenic determinant of a mutable pathogen) increases the mutation frequency of the subject nucleic acid to a rate that can approach or roughly approximate that naturally occurring in the immunoglobulin variable region.

Exemplary hypermutability elements include immunoglobulin enhancers, including the heavy chain large intronic enhancer (Iglin) and the 3' kappa (K) enhancer. See e.g., Bachl, J. et al. (2001) *J Immunol* 166:5051-5057; Bachl, J. et al. (1999) *Proc Natl Acad Sci USA* 96:6847-6849; Bachl, J. et al. (1998) *Proc Natl Acad Sci USA* 95:2396-2399; U.S. Pat No. 5,885,887. Enhancers and hypermutation-active portions thereof are functionally interchangeable for the invention. Thus, an Iglin enhancer can be the XbaI-EcoRI fragment described in Grosschedl et al. (1985) *Cell* 41:885-897, and can be portions thereof that have somatic hypermutation activity. A K enhancer can be the ScaI-XbaI fragment described in Meyer et al. (1989) *EMBO J*. 8:1959-1964, and can be portions thereof that have somatic hypermutation activity. Portions of enhancers that have somatic hypermutation activity can be identified, for example, by deletional analysis (i.e., making nucleic acid constructs containing enhancer deletion mutants and a reporter gene and determining the rate of mutation of the reporter gene). Deletion mutants can be prepared, for example, by chemical or enzymatic synthesis, or by exonuclease treatment of enhancers.

In one aspect of the invention, a nucleic acid construct contains one or more copies of an Iglin enhancer and/or one or more copies of a K enhancer. In some embodiments, a nucleic acid construct contains either a single Iglin enhancer or a single K enhancer. In other embodiments, a nucleic acid construct contains a single Iglin enhancer and a single K enhancer. In other embodiments, a nucleic acid construct contains multiple Iglin enhancers or multiple K enhancers. In other embodiments, a nucleic acid construct contains multiple Iglin enhancers and multiple K enhancers. In another embodiment, a nucleic acid construct contains a single Iglin enhancer and multiple K enhancers. In another embodiment, a nucleic acid construct contains multiple Iglin enhancers and a single K enhancer.

Enhancers can be positioned 3' or 5' relative to the subject nucleic acid, and can be positioned on a nucleic acid construct in either the 5' to 3' or the 3' to 5' orientation. Preferably, the enhancer is positioned 3' of the subject nucleic acid. The 5' end of an Iglin enhancer oriented 5' to 3' is typically positioned less than 5 kb (e.g., 0 to 1 kb, 1 to 2 kb, 2 to 3 kb, 3 to 4 kb, or 4 to 5 kb) from the 3' end of a subject nucleic acid. When an Iglin enhancer and a K enhancer are positioned 3' to the subject nucleic acid, the Iglin enhancer typically is positioned closer to the subject nucleic acid. In these embodiments, the 5' end of a K enhancer oriented 5' to 3', when present, is positioned less than 20 kb (e.g., 0 to 1 kb, 1 to 5 kb, 5 to 10 kb, 10 to 15 kb, and 15 to 20 kb) from the 3' end of an Iglin enhancer oriented 5' to 3'. A variety of configurations of enhancers is described in U.S. Pat. No. 5,885,827.

Somatic hypermutation activity and operable linkage to a subject nucleic acid can be determined by independently measuring the mutation rate of the subject nucleic acid in hypermutable B cells containing the construct and in non-hypermutable B cells containing the construct. In a nucleic acid construct that contains a hypermutability element operably linked to a subject nucleic acid, the subject nucleic acid typically exhibits a mutation rate at least two-fold higher in hypermutable B cells than in non-hypermutable B cells. The absolute mutation rate of a subject nucleic acid in such a construct is typically in the range of $1 \times 10^{-7}$ to $1 \times 10^{-4}$ (e.g., $1 \times 10^{-7}$ to $1 \times 10^{-6}$, $1 \times 10^{-6}$ to $1 \times 10^{-5}$, and $1 \times 10^{-5}$ to $5 \times 10^{-4}$) bp/cell/generation.

In some embodiments, a nucleic acid construct of the invention is a vector, such as a plasmid or viral vector, capable of trsporting an encoded antigenic determinant and hypermutability element into a host cell. Some vectors are capable of autonomously replicating in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell and are replicated with the host genome.

Expression vectors can direct the expression of one or more genes encoded thereon. Expression vectors can be, for example, plasmid vectors or viral vectors (e.g., replication defective retroviruses, adenoviruses and adeno-associated viruses). Expression vectors include one or more regulatory sequences, selected on the basis of the host cells to be used for expression, operatively linked to the nucleic acid to be expressed. With respect to regulatory elements, "operably linked" means that the nucleotide sequence to be expressed and regulatory sequence(s) are positioned in the expression vector such that nucleotide sequence is transcribed and translated (e.g., in an in vitro transcription/translation system or in a host cell when the vector is introduced into the host cell).

Regulatory sequences include promoters, enhancers and other expression control elements (e.g., polyadenylation signals). See e.g., Goeddel, Gene Expression Technology: Methods in Enzymology 185, Academic Press, San Diego, Calif. (1990). Regulatory sequences include those that direct constitutive expression of a nucleotide sequence in many types of host cells and that direct expression of the nucleotide sequence only in certain host cells (e.g., cell type or tissue-specific regulatory sequences). It will be appreciated by those skilled in the art that the design of the expression vector can depend on such factors as the choice of the host cell, the desired level of protein expression, the stability of the encoded product (MRNA or protein), and the intended use of the encoded protein (e.g., whether it will be isolated). Expression vectors of the invention can be introduced into host cells to produce proteins encoded by nucleic acids.

Expression vectors of the invention can be designed for expression of antigenic determinants in prokaryotic or eukaryotic cells (e.g., bacterial cells such as *E. coli*, insect cells, yeast cells and mammalian cells). Some suitable host cells are described below, and others are described in Goeddel, Gene Expression Technology: Methods in Enzymology 185, Academic Press, San Diego, Calif. (1990). Expression vector also can be transcribed and translated in vitro, for example using T7 promoter regulatory sequences and T7 polymerase.

Expression of proteins in prokaryotes is typically carried out with vectors containing constitutive or inducible promoters directing the expression of fusion or non-fusion polypeptides. Fusion polypeptides have additional amino acids ("tags") associated with either the N- or C-terminus of the antigenic determinant. Fusion expression vectors typically serve any of three purposes: 1) to increase expression of recombinant protein; 2) to increase the solubility of the recombinant protein; 3) to regulate the half life of the protein in the cell; 4) to increase antigenicity of the protein; and 5) to facilitate purification of the recombinant protein (e.g., by acting as a ligand in affinity purification). Typically, the additional amino acids are capable of binding a substrate-bound molecule, and the fusion polypeptide can be purified by washing unbound material from substrate-bound fusion polypeptides. Some fusion expression vectors encode as additional fusion amino acids the following purification tags: FLAG™ (U.S. Patent No. 4,851,341), 6×HIS, c-myc, Protein C, VSV-G, hemagglutinin, biotin, glutathione S-transferase (GST) (e.g., pGEX (Pharmacia Biotech Inc; Smith and Johnson (1988) *Gene* 67:3140), maltose E binding protein (e.g. pMAL (New England Biolabs, Beverly, Mass.), and protein A (e.g., pRIT5 (Pharmacia, Piscataway, N.J.)). To protect fusion polypeptides from somatic hypermutation, sequences encoding purification polypeptides are typically positioned 3' relative to hypermutation elements, and splice sites are provided so that the sequence encoding the purification polypeptide can be fused with the sequence encoding the antigenic determinant before translation. Often, in fusion expression vectors, a proteolytic cleavage site is introduced at the junction of the fusion moiety and the recombinant protein to enable separation of the recombinant protein from the fusion moiety subsequent to purification of the fusion protein. Such proteolytic enzymes include Factor Xa, thrombin and enterokinase.

One strategy to maximize recombinant protein expression in a prokaryote is to express the protein in a bacterial host having an impaired capacity to proteolytically cleave the recombinant protein (Gottesman, Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res*. 20:2111-2118). Such alteration of nucleic acid sequences of the invention can be carried out by standard molecular biology techniques.

Examples of *S. cerevisae* expression vectors include pYepSec 1 (Baldari et al. (1987) *EMBO J*. 6:229-234), pMFa (Kujan and Herskowitz, (1982) *Cell* 30:933-943), pJRY 88 (Schultz et al. (1987) *Gene* 54:113-123), pYES2 (Invitrogen Corporation, San Diego, Calif.), pGBT9 (Clontech, Palo Alto, Calif.), pGAD 10 (Clontech, Palo Alto, Calif.), pYADE4 and pYGAE2 and pYPGE2 (Brunelli and Pall (1993) *Yeast* 9:1299-1308), pYPGE15 (Brunelli and Pall (1993) *Yeast* 9:1309-1318), pACTII (Dr. S. E. Elledge, Baylor College of Medicine), and picZ (InVitrogen Corp, San Diego, Calif.). *Baculovirus* vectors available for expression of proteins in cultured insect cells (e.g., Sf 9 cells) include the pAc series (Smith et al. (1983) *Mol. Cell Biol*. 3:2156-2165) and the pVL series (Lucklow and Summers (1989) *Virology* 170:31-39). Exemplary mammalian expression vectors include pCDM 8 (Seed (1987) *Nature* 329:840), pCI (Promega), and pMT2PC (Kaufman et al. (1987) *EMBO J*. 6:187-195). When used in mammalian cells, the expression vector's control functions are often provided by viral regulatory elements. For example, commonly used promoters are derived from polyoma, Adenovirus 2, cytomegalovirus and Simian Virus 40. Other suitable expression systems for both prokaryotic and eukaryotic cells are described in Sambrook et al. Molecular Cloning—A Lab Manual. Ch. 16, 17 Cold Spr. Harbor Lab. Press, CSH, NY 1988.

In some embodiments, a recombinant mammalian expression vector is capable of directing expression of the nucleic acid preferentially in a particular cell type (e.g., cell type or tissue-specific regulatory elements are used to express the nucleic acid). Cell type or tissue-specific regulatory elements are known in the art. Tissue-specific promoters include the albumin promoter (liver-specific; Pinkert et al. (1987) *Genes Dev*. 1:268-277), lymphoid-specific promoters (Calame and Eaton (1988) *Adv. Immunol*. 43:235-275), in particular promoters of T cell receptors (Winoto and Baltimore (1989) *EMBO J*. 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters include the murine hox promoters (Kessel and Gruss (1990) *Science* 249:374-379) and the α-fetoprotein promoter (Campes and Tilghman (1989) *Genes Dev*. 3:537-546).

Cells

The invention also provides host cells containing a nucleic acid construct of the invention. Host cells are typically isolated (e.g., removed from an organism and/or cultured ex vivo). The term "host cell" refers to a prokaryotic or eukaryotic cell into which a nucleic acid construct has been introduced, and to the progeny of such a cell. Since mutation or environmental influences may cause modifications in succeeding generations, such progeny may not be identical to the parent cell, but are still within the meaning of the term "host cell."

Nucleic acid constructs of the invention can be introduced into a variety of host cells known to the skilled artisan (e.g., bacterial cells such as *E. coli*, insect cells, yeast or mammalian cells such as B cells). Nucleic acid constructs can be introduced into prokaryotic or eukaryotic cells via conventional transformation, transfection, or transduction techniques. As used herein, the terms "transformation" and "transfection" are intended to refer to a variety of art-recognized techniques for introducing nucleic acid (e.g., DNA) into a host cell, including calcium phosphate or calcium chloride co-precipitation, DEAE-dextran-mediated transfection, lipofection, and electroporation. Transduction refers to introduction of a nucleic acid construct in cells via infection by a viral vector.

In some embodiments, the host cells are hypermutable cells. Hypermutable B cells are cells of the B lineage (e.g., 1B5-S4 and 1B5-S2 cells) that contain trans-acting cellular factors that work in conjunction with cis-acting hypermutability elements to facilitate somatic hypermutation. Non-hypermutating cells do not sustain somatic hypermutation of sequences linked in cis to hypermutability elements (e.g. 70Z-S1 cells. Hypermutable cells include cells of pre-B lymphocyte origin, such as 18-81 cells (See e.g., U.S. Pat. No. 5,885,887) and cells described herein. Hypermutable cells can be constructed by expressing one or more genes that encode a trans-acting hypermutation factor in non-hypermutating cells. These trans-acting factors act upon sequences that are linked in cis to hypermutability elements. Such cells can be made, for example, by introducing a eDNA library or parts thereof into cells containing a cis-acting hypermutability element operably linked to a reporter gene. The cDNA can be prepared by conventional techniques from, for example, hypermutable B cells. Cells containing the introduced cDNA are grown to a desired density are screened for hypermutation mutants that express the reporter gene. Hypermutating cells can be cloned and cell lines established.

Depending upon the expression vector and technique used to transfect DNA into mammalian cells, a fraction of cells may integrate the DNA into their genome. In some cases, the host cell retains the entire DNA molecule while in other cases, the host cell retains a portion of the DNA molecule. To identify and select cells stably transfected with the introduced nucleic acid (i.e., integrants), a gene that encodes a selectable marker (e.g., resistance to antibiotics or drugs such as G418, hygromycin, puromycin, or methotrexate) is generally introduced into the host cells along with the gene of interest. A nucleic acid encoding a selectable marker can be introduced into a host cell on a nucleic acid construct of the invention or can be introduced on a separate nucleic acid. Integrants can be identified by drug selection (e.g., cells that have incorporated the selectable marker gene will survive, while the other cells die).

A host cell of the invention can be used to produce (i.e., express) an antigenic determinant encoded by a nucleic acid of the invention. Host cells containing a nucleic acid construct of the invention can be cultured in a suitable medium such that the encoded antigenic determinant is produced. The antigenic determinant can then be isolated from the medium or the host cell using known methodologies.

Methods for Making Variant Antigenic Polypeptides

Variant antigenic polypeptides can be produced by introducing a nucleic acid construct of the invention into a hypermutable cell or a mammal. Methods for introducing nucleic acid constructs into cells are described above. DNA can be introduced into a mammal by a variety of methods. For example, DNA can be incorporated into microparticles suited for administration to mammals. See, e.g., U.S. Pat. No. 6,270,795; WO-94/23738; and EP-A-0248531. Alternatively, WO-95/05853 describes methods, compositions and devices for injecting naked DNA encoding an immunogenic antigen with the aim of raising antibodies in the recipient of the naked DNA. Liposomal delivery of DNA has also been described.

See e.g., EP-A-0475178. Another method for obtaining in vivo expression of a desired gene product is described in EP-A-0161640, in which mammalian cells expressing a bovine growth hormone are encapsulated and implanted into a cow to increase milk production therein.

Known methodologies can be used to determine whether a hypermutable cell or mammal produces a variant of the antigenic determinant. For example, antigenic determinants can be isolated from cells or mammals (e.g., by immunoaffinity chromatography) and analyzed by two-dimensional SDS PAGE and Western blotting. A change in migration, in either direction, of the isolated antigenic determinant relative to that of the originally encoded antigenic determinant indicates that the cell or organism produces a variant. Alternatively, a nucleic acid encoding an antigenic determinant can be isolated and its sequence compared with that of the nucleic acid construct introduced into the cell or organism. Nucleic acids can be sequenced according to standard methods. A change in the nucleic acid sequence that alters the amino acid sequence of the encoded antigenic determinant relative to that of the originally encoded antigenic determinant indicates that the cell or organism produces a variant antigenic determinant.

Methods for Inducing an Immune Response and Producing Antibodies

In another aspect, the invention provides methods for inducing an immune response and producing antibodies. A nucleic acid construct of the invention can be introduced into a mammal as described above, then a variety of methods can be used to determine if an immune response has been induced. Methods for obtaining serum antibodies, and for assaying their reactivity toward antigens are well known. For example, serum antibodies can be analyzed before and after introduction of the nucleic acid construct into the mammal (e.g., by ELISA using antigenic determinants purified from supernatant(s) of hybridomas producing variant antigenic determinants). A mammal exhibits an immune response to a variant antigenic determinant if the serum antibodies of the mammal react with a particular variant, but did not react with this variant prior to introducing the nucleic acid construct.

The invention will be further described in the following examples, which do not limit the scope of the invention described in the claims.

EXAMPLES

Example 1

Targeted Somatic Hypermutation in B Cells

This example demonstrates that cis-acting sequence elements on a plasmid can target other nucleic acid sequences on the plasmid for somatic hypermutation in cells of the B lineage.

The pE plasmid, schematically illustrated in FIG. 1, contains a green fluorescent protein ("GFP") coding sequence modified to contain a TAG stop codon within its coding sequence and a poly(A) addition site following the GFP coding sequence. See, Bachl et al. (1999) Proc. Natl. Acad Sci. USA 96:6847-6849. The thymidine kinase promoter, PtK ("P") facilitates transcription of the GFP gene, and the immunoglobulin heavy chain large intronic enhancer ("Iglin") acts in cis as a hypermutability element. The pE plasmid also contains a puromycin resistance gene ("Puro") 3' to Iglin.

Figure 2:
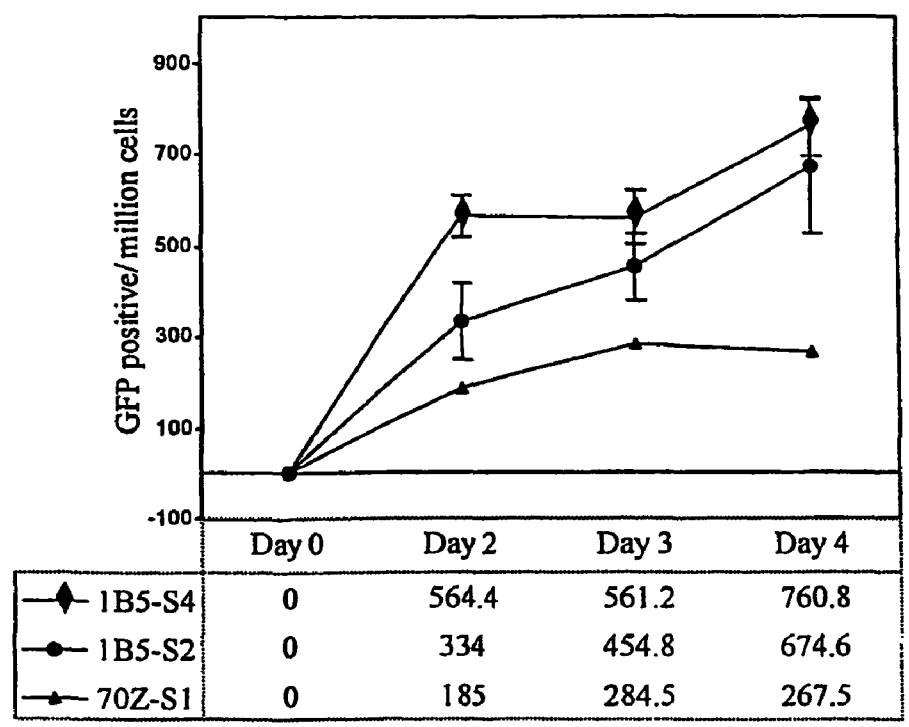
FIG. 2 is a chart showing somatic mutation rates.

The reversion rate of the stop codon in the GFP coding region of the pE plasmid was determined independently in hypermutating and non-hypermutating cell lines. See FIG. 2. 1B5-S4 and 1B5-S2 are clones of hypermutating B cell lines, and 70Z-S1 a clone of a non-hypermutating B cell line. 1B5-S2 and 1B5-S4 are subclones of 18-81 Pre-B cell lines. See, Siden et al. (1979) Cell 16:389-396; Burrows et al. (1981) PNAS 78: 564-568). 70Z-S1 is a subclone of the 70Z/3 line. See, Paige C et al. (1981) Nature 262: 631. For each cell line, $10^7$ cells were transfected with the pE plasmid. Transfectants were selected for puromycin resistance and amplified to a clonal size of approximately $10^7$ cells under conditions of unrestricted growth (no crowding). On day 0, 1-5×$10^6$ non-fluorescent cells were sorted and seeded (in quadruplicate for 1B5 clones and in duplicate for the 70Z-S1 clones) into 100 ml of fresh medium and expanded over the next 4 days. Each day a sample of each culture was analyzed for the presence of fluorescent cells (stop codon revertants) and non-fluorescent cells, and the frequency of GFP-positive cells arising over time after seeding was calculated and plotted. The 0.7×$10^4$ bp/cell/generation reversion rate of the GFP stop codon measured in the last two days agrees with independent measurements of the rate of somatic hypermutation measured in the same cell line.

Example 2

Hypermutable Nucleic Acid Construct

Plasmid pHAMut contains a hemaglutinin (HA) gene fused to 3 complement C3d coding sequences, obtainable as a BamHI-HindIII fragment from plasmid sHA-3C3d (Ross et al. (2000) Nature Immunology 1:127-131). The HA-3C3d gene fusion is cloned into Bluescript (Stratagene). The PtK promoter (obtainable from pMC1 Neo (Stratagene) fragment 455-733) and the immunoglobulin heavy chain large intronic enhancer ("Iglin") (obtainable as a 1Kb XbaI fragment of pµ132, Grosschedl et al. (1984) Cell 38:647-658) are cloned 5' and 3' of the HA-3C3d gene fusion, respectively, and are oriented and positioned as they are in plasmid pE. Plasmid pHAMut also contains, 3' of the Iglin enhancer, the 3' end of the immunoglobulin heavy chain gamma constant genomic region from the C2 exon to the membrane exons (obtainable by PCR amplification of mouse genomic DNA), a poly(A) addition site, and a yellow fluorescent protein (YFP) coding sequence.

Transfection and transduction efficiency are determined by YFP expression. In YFP positive cells, hypermutability of the HA gene in pHAmut is tested by nucleic acid sequencing. Hypermutability is assessed by comparison between the sequences obtained and the original HA gene sequence. Viral proteins produced by pHAmut are tested for variation after purification by affinity chromatography or immunoprecipitation followed by 2D SDS-PAGE and Western Blotting. Cells producing mutant forms of HA can be cloned.

Example 3

B Cell Transfectants

Plasmid pHAMut is transfected into mouse B cells and adoptively transferred into congenic recipients. Transfection and transduction efficiency is calculated by determining the frequency of yellow fluorescent recipients. HA expression by YFP-positive B cells is analyzed by RT-PCR of HA RNA and immunoprecipitation of HA protein.

Example 4

Vaccination of Mammals

Vaccination of mammals (e.g. mice) is accomplished by injecting pHAmut transfected/transduced B cells into the tail vein of congenic recipients. Vaccinated mice may be optionally immunized with an influenza unrelated antigen (e.g. NP-ovalbumin). Analysis of the expression of the viral antigens encoded by the pHAmut is performed before and after cell transfer (if immunization is done, analysis after transfer will be on day 21 post-immunization).

Wild type and mutant HA proteins are detected by a standard ELISA assay. An increase in the HA titer following vaccination indicates that transduced B cells produce HA in vivo. Expression of mutant forms of HA is analyzed in the serum of vaccinated animals by immunoprecipitation followed by 2D SDS-PAGE and western blotting. Hybridomas are also produced using splenocytes of immunized mice expressing HA in the serum. Hypermutation of the HA gene in vivo in vaccinated animals is confirmed by sequencing the HA gene in the hybridomas producing the mutant HA forms and in YFP positive B220-negative B cells obtained from vaccinated animals.

Immune response to the wild type and HA mutant forms is analyzed by ELISA of serum antibodies before and after vaccination using mutant HA proteins purified from hybridoma supernatants. A finding that mice vaccinated with B cells containing the pHAmut vector make antibodies directed against distinct HA variants more frequently and with higher relative avidity than mice vaccinated with B cells containing a mock vector indicates that pHAmut directs hypermutation of HA, and that mice containing pHAMut can develop an antibody response against HA variants.

To determine whether pHAmut can provide protection from various strains of influenza, mice are reconstituted with B cells containing or lacking pHAMut, optionally immunized with a non-influenza antigen, and infected with influenza containing the HA allele encoded on pHAmut. Parallel experiments are performed using influenza strains containing different HA alleles. A finding that $LD_{50}$ measurements for the various HA alleles is statistically higher for immunized mice reconstituted with B cells containing pHAMut than for immunized mice reconstituted with B cells lacking pHAMut indicates that mice containing pHAMut can develop a protective antibody response against HA variants (i.e., that pHAMut can confer protection against newly encountered or arising influenza strains).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making variant antigenic polypeptides in a mammal, said method comprising:
   a) introducing a nucleic acid construct into a hypermutable B cell, wherein said nucleic acid construct comprises a nucleic acid encoding an antigenic determinant of a mutable pathogen operably linked to: i) a promoter, ii) one or more complement C3d coding sequences, and iii) one or more hypermutability elements; and
   b) introducing said hypermutable B cell into said mammal such that variants of said antigenic determinant are expressed in said mammal.

2. The method of claim 1, wherein said antigenic determinant is an influenza hemaglutinin polypeptide.

3. A method for inducing an immune response in a mammal, said method comprising:
   a) introducing a nucleic acid construct into a hypermutable B cell, wherein said nucleic acid construct comprises a nucleic acid encoding an antigenic determinant of a mutable pathogen operably linked to: i) a promoter, ii) one or more complement C3d coding sequences, and iii) one or more hypermutability elements; and
   b) introducing said hypermutable B cell into said mammal such that variants of said antigenic determinant are expressed in said mammal,
   whereby an immune response against said variants of said antigenic determinant is induced in said mammal.

* * * * *